United States Patent
Cho et al.

(10) Patent No.: US 9,271,679 B2
(45) Date of Patent: Mar. 1, 2016

(54) METHOD AND APPARATUS FOR PROCESSING MEDICAL IMAGE SIGNAL

(71) Applicants: SAMSUNG ELECTRONICS CO., LTD., Suwon-si (KR); Korea University Research and Business Foundation, Seoul (KR)

(72) Inventors: Hyug-rae Cho, Seoul (KR); Yong-Hwan Kim, Seoul (KR); Hei-soog Kim, Anyang-si (KR); Jong-Hwan Lee, Seoul (KR)

(73) Assignees: SAMSUNG ELECTRONICS CO., LTD., Suwon-si (KR); Korea University Research and Business Foundation, Seoul (KR)

( * ) Notice: Subject to any disclaimer, the term of this patent is extended or adjusted under 35 U.S.C. 154(b) by 93 days.

(21) Appl. No.: 13/974,397

(22) Filed: Aug. 23, 2013

(65) Prior Publication Data

US 2015/0030220 A1    Jan. 29, 2015

(30) Foreign Application Priority Data

Jul. 24, 2013  (KR) .................. 10-2013-0087609

(51) Int. Cl.
G06K 9/00    (2006.01)
A61B 5/00    (2006.01)
A61B 5/1455  (2006.01)

(52) U.S. Cl.
CPC .............. *A61B 5/725* (2013.01); *A61B 5/0042* (2013.01); *A61B 5/14553* (2013.01)

(58) Field of Classification Search
None
See application file for complete search history.

(56) References Cited

U.S. PATENT DOCUMENTS

| 2003/0093004 | A1 | 5/2003 | Sosa et al. | |
|---|---|---|---|---|
| 2008/0241839 | A1 | 10/2008 | Potkin et al. | |
| 2010/0174171 | A1 | 7/2010 | Lee et al. | |
| 2011/0004110 | A1 | 1/2011 | Shusterman | |
| 2013/0034277 | A1* | 2/2013 | Cecchi et al. | 382/128 |
| 2013/0138182 | A1* | 5/2013 | Nissila et al. | 607/88 |

FOREIGN PATENT DOCUMENTS

JP   2009-297382 A   12/2009
KR   10-2012-0050379 A   5/2012

OTHER PUBLICATIONS

Communication dated Jan. 28, 2015 issued by the Korean Intellectual Property Office in counterpart Application No. 10-2013-0087609.
Xi-Nian Zuo et al., "Reliable intrinsic connectivity networks: Test-retest evaluation using ICA and dual regression approach", NeuroImage, 2010, pp. 2163-2177.
M.Venu Gopala Rao et al., "Local Adaptive Bivariate Shrinkage Function for Medical Image Denosing", International Journal of Electronics Engineering, 2009, pp. 59-65.
Communication dated Jul. 20, 2015 issued by Korean Intellectual Property Office in counterpart Korean Patent Application No. 10-2013-0087609.

* cited by examiner

*Primary Examiner* — Atiba O Fitzpatrick
(74) *Attorney, Agent, or Firm* — Sughrue Mion, PLLC (57) ABSTRACT

A method of processing a medical image signal includes estimating first time courses and first spatial patterns for a group of objects from first brain function data for the group, and estimating second time courses and second spatial patterns for a target object from second brain function data obtained from the target object by using the first time courses and the first spatial patterns.

23 Claims, 8 Drawing Sheets

METHOD AND APPARATUS FOR PROCESSING MEDICAL IMAGE SIGNAL

CROSS-REFERENCE TO RELATED APPLICATION

This application claims priority from Korean Patent Application No. 10-2013-0087609, filed on Jul. 24, 2013, in the Korean Intellectual Property Office, the disclosure of which is incorporated herein in its entirety by reference.

BACKGROUND

1. Field

Apparatuses and methods consistent with exemplary embodiments relate to a method and apparatus for processing a medical image signal, and more particularly, to a method and apparatus capable of estimating brain function activation patterns from brain function data obtained by a medical imaging apparatus.

2. Description of the Related Art

Representative examples of non-invasive measurement techniques include, for example, functional magnetic resonance imaging (fMRI), positron emission tomography (PET), and magnetoencephalography (MEG). Among the techniques, the fMRI has a higher spatial resolution and is widely used. The fMRI is also used to measure various physical quantities, image the measured various physical quantities for detecting an activated region of a brain, and effectively predict brain functions. More specifically, the fMRI captures a cross-section image of a brain that shows a dynamic situation such as, for example, a flow of oxygen in the brain.

When an activity of a particular region of a brain such as neural cells increases so that the region becomes active with increased a metabolic activity, a blood flow supply to a capillary vessel in the region increases, thereby resulting in an increase in a percentage of hemoglobin bound to oxygen within a blood. Hemoglobin bound to oxygen in an activated tissue has a higher signal intensity than hemoglobin which is not been bound to oxygen in surrounding tissues. A signal used to detect such a signal intensity difference is called a blood-oxygenation-level-dependent (BOLD) signal.

The fMRI method measures activation patterns of a desired region of a brain by detecting a BOLD signal and constructing the BOLD signal into a two-dimensional (2D) image. Since it requires about 1 to about 3 seconds to perform a brain scan, a plurality of brain scans may require a period of about 20 to about 30 seconds during which a predetermined task is performed. Examples of the predetermined task may include scanning a participant's brain while under an influence of specific stimuli, thoughts, and exercises.

Thus, the fMRI method continuously measure changes in a magnetic resonance (MR) signal to identify a part of a brain where intensity of the MR signal is increased in response to external stimuli and determine the identified part as an activated region of the brain. That is, the fMRI method measures a degree of functional brain activation by repeatedly measuring the BOLD signal when a brain is activated.

The fMRI uses the same basic principles as MRI in that an anatomical structure of a brain is imaged to reflect a photon density in tissues in vivo, a longitudinal relaxation time, and a transverse relaxation time. However, unlike the MRI, the fMRI additionally measures a local increase in a blood flow in an active region of a brain and a BOLD signal in response thereto. Thus, the fMRI may be used to detect a brain function region (i.e., activated region of a brain) associated with a predetermined task based on a change in a BOLD signal while a participant performs the task. Statistical parametric mapping (SPM) based on a general linear model and an independent component analysis (ICA) may be used to interpret time series data of the BOLD signal measured with the fMRI. In particular, the ICA is a data-driven analysis method that can detect a brain function area without prior information about a task performed by a participant. When applying the ICA method to fMRI data, there is a need for a technique of estimating brain function activation patterns from a BOLD signal with higher accuracy.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide a method and an apparatus for processing a medical imaging signal, in which performance of analyzing brain function activation patterns associated with a predetermined task and determining whether a participant's brain functions normally may be improved.

According to an aspect of an exemplary embodiment, there is provided a method of processing a medical image signal including: estimating first time courses and first spatial patterns for a group of objects from first brain function data for the group; and estimating second time courses and second spatial patterns for a target object from second brain function data obtained from the target object by using the first time courses and the first spatial patterns.

The estimating the second time courses and the second spatial patterns may include iteratively estimating time courses $A_k(i)$ and spatial patterns $S_k(i)$ for the target object from the second brain function data by using previously estimated time courses $A_{k-1}(i)$ and spatial patterns $S_{k-1}(i)$ for the target object, wherein the first time courses and the first spatial patterns are used as initial values $A_0(i)$ and $S_0(i)$ of the estimated time courses and spatial patterns for the target object respectively, and wherein the estimating of the time courses $A_k(i)$ and the spatial patterns $S_k(i)$ is iterated until a at least one from among difference between the previously estimated time courses $A_{k-1}(i)$ and the estimated time courses $A_k(i)$ and a difference between the previously estimated spatial patterns $S_{k-1}(i)$ and the estimated spatial patterns $S_k(i)$ fall within a range.

The estimating the second time courses and the second spatial patterns may include iteratively estimating time courses $A_k(i)$ and spatial patterns $S_k(i)$ for the target object from the second brain function data by using previously estimated time courses $A_{k-1}(i)$ and spatial patterns $S_{k-1}(i)$ for the target object. In this case, the first time courses and the first spatial patterns may be used as initial values $A_0(i)$ and $S_0(i)$ of the estimated time courses and spatial patterns for the target object, respectively, and the estimating of the time courses $A_k(i)$ and the spatial patterns $S_k(i)$ for the target object may be iterated a number of times.

The estimating the second time courses and the second spatial patterns may include estimating the second time courses from the second brain function data, the first time courses, and the first spatial patterns and estimating the second spatial patterns from the second brain function data and the second time courses.

The estimating the second time courses and the second spatial patterns may further include refining the estimated second spatial patterns to maximize independence of each spatial pattern included in the second spatial patterns.

The method for processing a medical image signal may further include displaying the second time courses and the second spatial patterns.

The estimating the first time courses and the first spatial patterns may include estimating the first time courses and the first spatial patterns by using a temporal concatenation group independent concatenation analysis (TC-GICA).

The estimating the first time courses and the first spatial patterns may include generating the first brain function data by concatenating brain function data obtained from each of the objects along a time axis and estimating the first time courses and the first spatial patterns from the first brain function data by using an independent concatenation analysis (ICA).

Each of the first brain function data and the second brain function data may include blood oxygenation level dependent (BOLD) data obtained by using a functional magnetic resonance imaging (fMRI) method.

The method of processing a medical image signal may further include acquiring spatial patterns obtained from a group of normal participants as reference activation patterns and determining whether second spatial patterns determined as activation patterns for the target object are normal based on a similarity between the reference activation patterns and the determined second spatial patterns.

According to an aspect of another exemplary embodiment, there is provided an apparatus for processing a medical image signal, including a group-level data analysis processor configured to estimate first time courses and first spatial patterns for a group of objects from first brain function data for the group; and an individual-level data analysis processor configured to estimate second time courses and second spatial patterns for a target object from second brain function data obtained from the target object by using the first time courses and the first spatial patterns.

The individual-level data analysis processor may use the first time courses and the first spatial patterns as initial values $A_0(i)$ and $S_0(i)$ of time courses and spatial patterns estimated for the target object, respectively, and iteratively estimating time courses $A_k(i)$ and spatial patterns $S_k(i)$ for the target object from the second brain function data by using previously estimated time courses $A_{k-1}(i)$ and spatial patterns $S_{k-1}(i)$ for the target object until at least one from among a difference between the previously estimated time courses $A_{k-1}(i)$ and the estimated time courses $A_k(i)$ and a difference between the previously estimated spatial patterns $S_{k-1}(i)$ and the estimated spatial patterns $S_k(i)$ fall within a range.

The individual-level data analysis processor may use the first time courses and the first spatial patterns as initial values $A_0(i)$ and $S_0(i)$ of time courses spatial and patterns estimated for the target object, respectively, and iteratively estimates, a number of times, time courses $A_k(i)$ and spatial patterns $S_k(i)$ for the target object from the second brain function data by using previously estimated time courses $A_{k-1}(i)$ and spatial patterns $S_{k-1}(i)$ for the target object.

The individual-level data analysis processor may estimate the second time courses from the second brain function data, the first time courses, and spatial patterns, and estimate the second spatial patterns from the second brain function data and the second time courses.

The individual-level data analysis processor may further refine the estimated second spatial patterns to maximize independence of each spatial pattern included in the second spatial patterns.

The apparatus for processing a medical image signal may further include a display configured to display the second time courses and the second spatial patterns.

The group-level data analysis processor may estimate the first time courses and the first spatial patterns by using a TC-GICA.

The group-level data analysis processor may generate the first brain function data by concatenating brain function data obtained from each of the objects along a time axis and estimate the first time courses and the first spatial patterns from the first brain function data by using an independent concatenation analysis (ICA).

Each of the first brain function data and the second brain function data may include BOLD data obtained by using an fMRI method.

The individual-level data analysis processor may acquire spatial patterns obtained from a group of normal participants as reference activation patterns, and determine whether second spatial patterns determined as activation patterns for the target object are normal based on a similarity between the reference activation patterns and the determined second spatial patterns.

According to an aspect of still an exemplary embodiment, there is provided a non-transitory computer-readable recording medium having recorded thereon a program for executing the above method of processing a medical image signal.

According to an aspect of still another exemplary embodiment, there is provided an apparatus for processing a medical image signal including a controller configured to estimate individual-level time courses and corresponding individual-level spatial patterns from group-level function data of a target object, wherein the controller iteratively estimates the individual-level time courses and the individual-level spatial patterns from individual-level function data of the target object using previously estimated time courses and spatial patterns for the target object until the estimated spatial patterns converge within a threshold.

BRIEF DESCRIPTION OF THE DRAWINGS

The above and/or other aspects will become more apparent by describing certain exemplary embodiments with reference to the accompanied drawings in which.

DETAILED DESCRIPTION

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Although the terms used herein are generic terms which are currently widely used and are selected by taking into consideration functions thereof, the meanings of the terms may vary according to the intentions of persons skilled in the art, legal precedents, or the emergence of new technologies. Furthermore, some specific terms may be randomly selected by the applicant, in which case the meanings of the terms may be specifically defined in the description. Thus, the terms should be defined not by simple appellations thereof but based on the meanings thereof and the context of the description. As used herein, the term "and/or" includes any and all combinations of one or more of the associated listed items. Expressions such as "at least one of," when preceding a list of elements, modify the entire list of elements and do not modify the individual elements of the list.

It will be understood that when the terms "includes," "comprises," "including," and/or "comprising," when used in this specification, specify the presence of stated elements and/or components, but do not preclude the presence or addition of one or more elements and/or components thereof. As used herein, the term "module" refers to a unit that can perform at least one function or operation and may be implemented utilizing any form of hardware, software, or a combination thereof.

Throughout the specification, the term "object" may mean a living or non-living thing to be represented as an image. The term "object" may also refer to a portion of a human body or a cross-section of the human body in a human body or animal. For example, the object may include a brain, but is not limited thereto.

The term "user" means a medical expert and includes, but is not limited to, a doctor, a nurse, a medical technologist, a sonographer, and a medical imaging expert.

The term "brain function data" means data that are used to detect a region of a brain activated in response to a predetermined task and may include, for example, blood-oxygenation-level-dependent (BOLD) data.

In this specification, the term "brain function activation pattern" may mean an aspect of brain activation in response to a predetermined task, which is obtained from brain function data.

The term "brain function spatial activation pattern" (hereinafter, referred to as a "spatial pattern" (SP)) refers to an aspect of activation in at least a region of a brain at a predetermined time in response to a predetermined task.

The term "brain function temporal activation pattern" (hereinafter referred to as a "time course" (TC)) may mean an aspect of activation in a particular region of a brain over time during performance of a predetermined task.

The term "predetermined task" may include allowing a participant to experience a particular stimulus, to engage in a particular thought, and carry out a particular exercise, but is not limited thereto. For example, the predetermined task may include allowing the participant not to be exposed to an external stimulus.

According to exemplary embodiments, when analyzing BOLD data measured when a participant performs a predetermined task, brain function activation patterns of the participant associated with the task may be more accurately analyzed.

A functional Magnetic Resonance Imaging (fMRI) apparatus is used to measure a change in a BOLD signal while a participant performs a predetermined task. Statistical parametric mapping (SPM) based on a general linear model and independent component analysis (ICA) are widely used for interpretation of time series data of a BOLD signal measured with the fMRI apparatus.

A method of applying fMRI data may be an individual ICA or a temporal-concatenation group ICA (TC-GICA). The individual ICA is an individual-level analysis method that applies ICA using the individual's BOLD data. The TC-GICA is a group-level analysis method that applies ICA using data generated by concatenating multiple individuals' BOLD data along a time axis.

The individual ICA method allows analysis of brain function activation patterns for each individual, but requires additional post-processing to find patterns that coincide with group-level activation patterns among the individual's brain function activation patterns. Furthermore, since additionally post-processed brain function activation patterns still have BOLD noise unique to each individual, it may be difficult to define patterns that coincide with the group-level activation patterns.

To overcome the above drawbacks of the individual ICA method, the TC-GICA method includes estimating group-level brain function activation patterns having reduced noise generated according to unique characteristics of each individual and estimating brain function activation patterns for each individual from the individual's BOLD data by using the group-level brain function activation patterns.

A dual-regression (DR) approach may be used to analyze each individual's SPs and corresponding TCs for group-level brain function activation patterns by using group-level SPs estimated by using a TC-GICA algorithm.

According to a related art method of processing a medical image signal using a DR approach, it is easier to find individual-level ICs related to a task among estimated group-level ICs, i.e., brain function activation patterns. However, since the estimated brain function activation patterns are greatly affected by noise present in the individual's BOLD data, the related art method provides lower performance in analysis for estimating each individual's brain function activation patterns.

Thus, a method of processing a medical image signal according to an exemplary embodiment applies an iterative DR approach employing "spatial sparseness" of individual' SPs to estimate brain function activation patterns from brain function data with higher accuracy. Thus, detection of a participant's activated brain function region associated with a predetermined task and diagnosis of abnormalities in the object's brain function activation patterns may become more accurate.

To analyze BOLD data measured while a participant performs a predetermined task, there is a need for a technique to easily and accurately estimate the participant's brain function activation patterns including a brain function associated with the task based on a predetermined normalized group-level template.

According to an exemplary embodiment, the normality of a participant's brain function activation patterns may be assessed by determining brain function activation patterns associated with the same task and acquired from normal participants as a template.

Exemplary embodiments will now be described in detail with reference to the accompanying drawings.

Figure 1A:
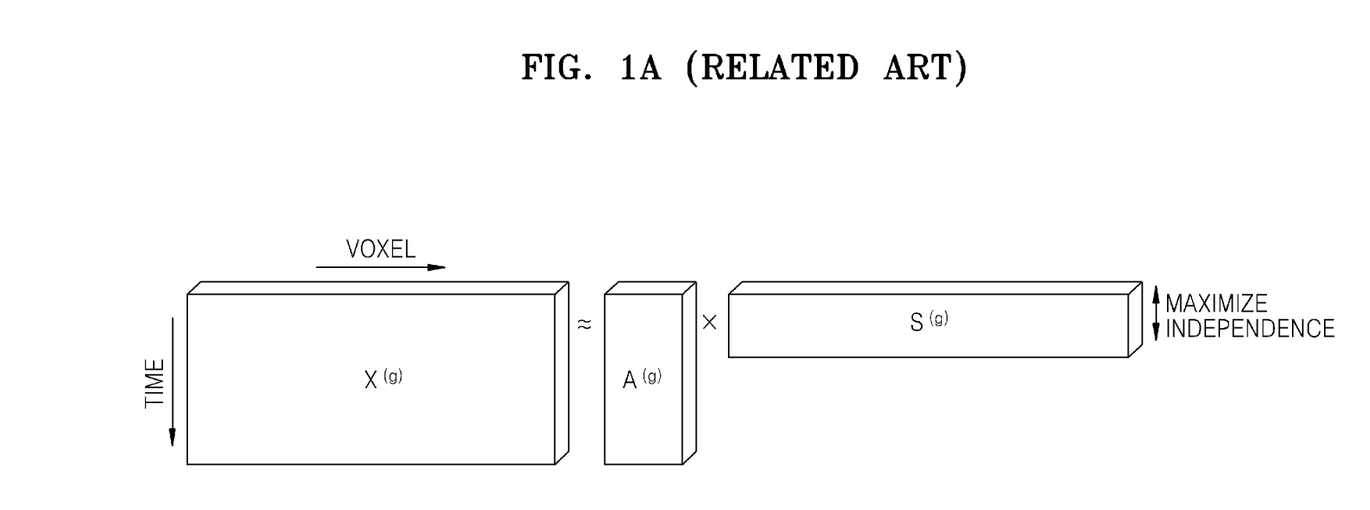
FIGS. 1A, 1B, and 1C are schematic diagrams for explaining a method of estimating brain function activation patterns using a related art dual-regression (DR) approach.
Figure 1B:
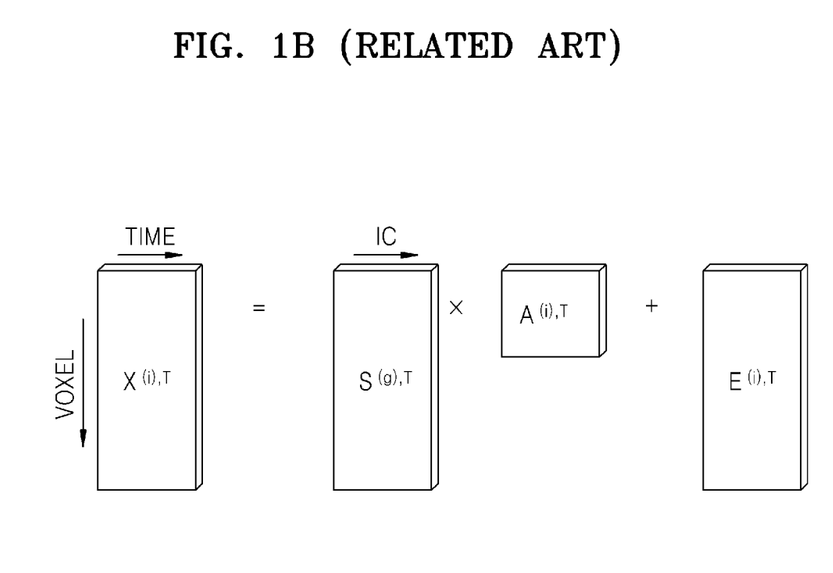
Figure 1C:
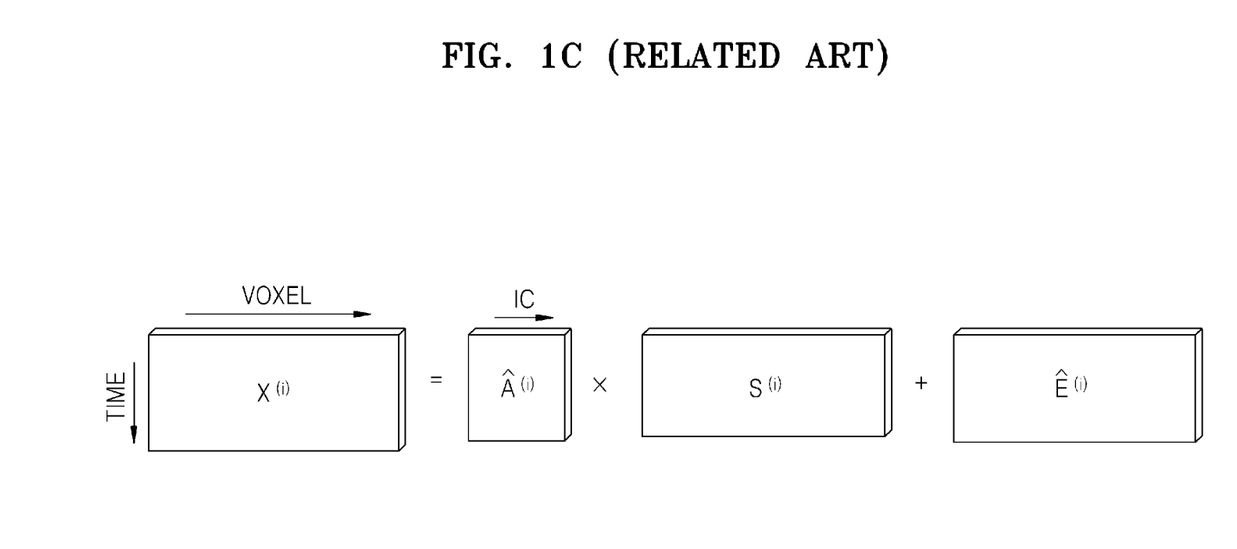

FIGS. 1A through 1C are schematic diagrams for explaining a method of estimating brain function activation patterns using a related art DR approach.

FIG. 1A is a schematic diagram for explaining a related art TC-GICA method used to estimate group-level brain function activation patterns from group-level brain function data. The TC-GICA method may be applied to a plurality of objects.

According to the TC-GICA method, an ICA method may be applied to group brain function data generated by concatenating brain function data acquired from each of a plurality of objects along a time axis.

Figure 5A:
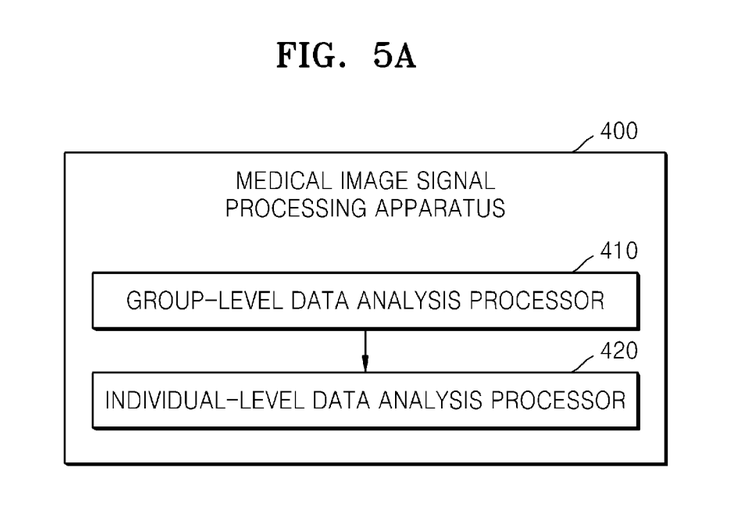
FIGS. 5A and 5B are block diagrams illustrating an apparatuses for processing a medical image signal according to exemplary embodiments.

More specifically, an apparatus (400 in FIG. 5) for processing a medical image signal generates a TC BOLD data matrix and applies the ICA to the TC BOLD data matrix to estimate group-level SPs and group-level TCs as independent components (ICs).

Column vectors of the TC BOLD data matrix may be BOLD time-series for all voxels within a brain area for each object. The matrix of TC BOLD data is generated by concatenating all voxels within a brain area for each object across all objects along the time axis. In other words, the TC BOLD data matrix has a time by voxels matrix format.

The ICs including group-level TCs and group-level SPs may be estimated by maximizing independence among SPs using an ICA algorithm.

In FIG. 1A, X(g) denotes a TC BOLD data matrix. As defined in Equation (1) below, the TC BOLD data matrix may be generated by concatenating BOLD time-series for all objects along a time axis.

$$X(g)=A(g)S(g)$$

$$(X(g)=[X(1)^T X(2)^T \ldots X(M)^T]^T) \quad (1)$$

wherein X(i) (i=1, 2, ... M) denotes BOLD time-series for an i-th object. As shown in Equation (1), the TC BOLD data matrix X(g) may be obtained by multiplying independent group-level SPs, S(g), by corresponding group-level TCs, A(g).

Thus, the group-level SPs, S(g), and the group-level TCs, A(g), may be estimated from the TC BOLD data matrix X(g) by maximizing independence among individual SPs contained in the group-level SPs.

FIG. 1B is a schematic diagram for explaining a method of estimating individual-level TCs by using group-level SPs as a regressor.

In FIG. 1B, X(i) is a BOLD data matrix for an i-th object, S(g) is group-level SPs, A(i) is individual-level TCs for the i-th object, and E(i) is a residual noise.

As defined in Equation (2) below, the individual-level TCs A(i) may be obtained from at least square (LS) algorithm, in which group-level SPs S(g) is used as a regressor to each individual's BOLD data while minimizing a residual error.

$$A(i)=X(i)S(g)^T(S(g)S(g)^T)^{-1} \quad (2)$$

FIG. 1C is a schematic diagram for explaining a method of estimating individual-level SPs by using individual-level TCs as a regressor.

In FIG. 1C, Â(i) is normalized so that the individual-level TCs A(i) estimated by using Equation (1) above have a zero-mean and a unit-variance. S(i) and Ê(i) represent individual-level SPs, and residual noise, respectively.

As defined in Equation (3) below, the individual-level SPs S(i) may be obtained from an LS algorithm, which uses individual-level TCs A(i) as a regressor to each individual's BOLD data while minimizing a residual error.

$$S(i)=(\hat{A}(i)^T\hat{A}(i))^{-1}\hat{A}(i)^T X(i) \quad (3)$$

The related art DR approach described with reference to FIG. 1A through 1C may find individual-level ICs based on group-level ICs, i.e., brain function SPs and TCs. However, this approach has a drawback in that the estimated individual-level brain function activation patterns are greatly affected by noise present in the individual's BOLD data, thereby providing lower performance in analysis for estimating each individual's brain function activation patterns.

According to an exemplary embodiment, the performance in analysis of brain function activation patterns may be improved compared to the related art DR approach.

Figure 2:
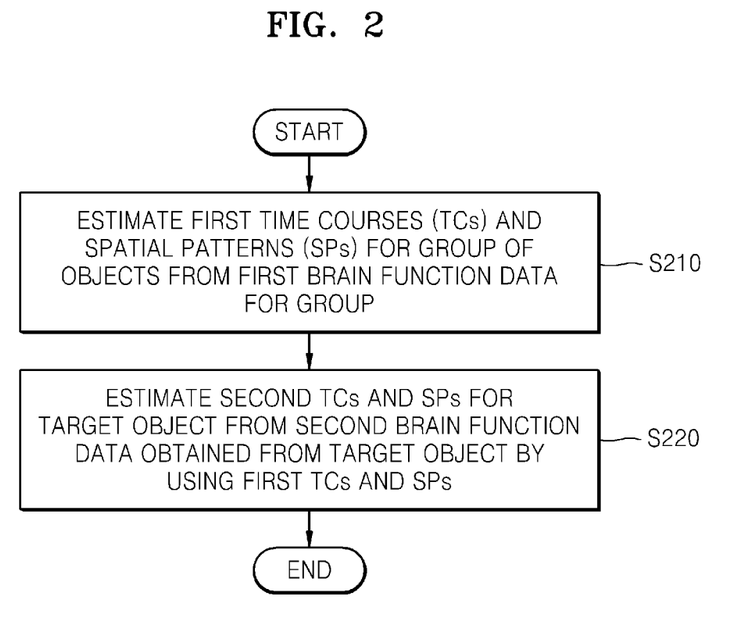
FIG. 2 is a flowchart illustrating a method of processing a medical image signal according to an exemplary embodiment.

FIG. 2 is a flowchart of a method of processing a medical image signal according to an exemplary embodiment.

For example, the method of processing a medical image signal according to an exemplary embodiment may include a technique for processing BOLD data obtained using fMRI.

The apparatus 400 for processing a medical image signal according to an exemplary embodiment may estimate first TCs and first SPs for a group of a plurality of objects from first brain function data for the group (S210).

In this regard, the apparatus 400 uses a TC-GICA method to estimate the first TCs and the first SPs for the group.

More specifically, the apparatus 400 generates a TC BOLD data matrix and applies an ICA method to the TC BOLD data matrix to estimate the first TCs and the first SPs for the group as ICs.

Column vectors of the TC BOLD data matrix may be BOLD time-series for all voxels within a brain area for each object. The TC BOLD data matrix may be generated by concatenating BOLD time-series for each object along a time axis. In other words, the TC BOLD data matrix has a time by voxels matrix format.

ICs including the first TCs and the first SPs may be estimated by maximizing independence among SPs using an ICA algorithm.

Since operation S210 may correspond to the TC-GICA method described above with reference to FIG. 1A, repeated descriptions with respect to FIG. 1A will be omitted to avoid redundancy.

The apparatus 400 may estimate second TCs and second SPs for a target object from second brain function data obtained from the target object by using the first TCs and SPs in operation S220.

In this case, the "target object" means an object for which a user intends to obtain brain function activation patterns.

The apparatus 400 applies a DR approach to the first TCs and SPs acquired in the operation S210 to estimate the second TCs and SPs.

To this end, the apparatus 400 estimates the second TCs for the target object from the second brain function data for the target object and the first TCs and SPs for the group. Next, the apparatus 400 may estimate the second SPs for the target object from the second brain function data for the target object and the second TCs for the target object.

In addition, the apparatus 400 may refine the estimated second SPs to maximize spatial sparsity of the second SPs across entire brain regions.

Refining the estimated second SPs to maximize their spatial sparseness may mean that the second SPs are organized to have sparse properties by applying a Laplacian probability density function (pdf) to maximize the independence of each of the second SPs.

The apparatus 400 according to an exemplary embodiment iteratively performs the operation S220 of estimating the second TCs and SPs for the target object from the second brain function data obtained from the target object.

In one exemplary embodiment, in the iteratively estimating of the second SPs and TCs, the apparatus 400 may iteratively perform the operation of estimating activation patterns for the target object until a difference between the second TCs estimated in the previous iteration and newly estimated second TCs or a difference between the second SPs estimated in the previous iteration and newly estimated SPs falls within a preset range. The apparatus 400 may determine whether a difference between the second TCs estimated in the previous iteration and the newly estimated second TCs or a difference between the second SPs estimated in the previous iteration and the newly estimated SPs falls within the preset range.

In this case, the apparatus 400 may acquire the third brain function data from the estimated second TCs and SPs. The third brain function data may be reconstructed from a linear combination of the second TCs and SPs.

The apparatus 400 may determine whether a normalized difference between the second and third brain function data for the target object falls within a preset range that is less than approximately, for example, 0.01. The preset range may vary depending on, for example, characteristics of the brain function data.

In this case, the preset range may be input from a user or may be a prestored value. The preset range may also vary adaptively with measured or estimated results, e.g., at least one of the first TCs and SPs, the second TCs and SPs, and the second brain function data.

For example, the apparatus 400 may determine that the difference falls within the preset range when a normalized difference between activation patterns estimated in the previous iteration and newly estimated activation patterns is less than or equal to a learning rate, e.g., 0.01.

When the normalized difference between the activation patterns estimated in the previous iteration and newly estimated activation patterns is less than the learning rate, the extent to which activation patterns to be subsequently estimated vary is less than the learning rate.

The apparatus 400 according to an exemplary embodiment may determine the first TCs and the first SPs as initial values $A0(i)$ and $S0(i)$ of the TCs and SPs estimated for the target object, respectively, and iteratively perform an operation of estimating activation patterns for the target object until a difference between TCs, $A_{k-1}(i)$, estimated in the previous iteration and newly estimated TCs, $A_k(i)$, and/or a difference between SPs, $S_{k-1}(i)$, estimated in the previous iteration and newly estimated SPs, $S_k(i)$, falls within a preset range.

For illustrative purposes, it is determined whether a difference between TCs, $A_{k-1}(i)$, estimated in a k−1-th iteration and TCs, $A_k(i)$, estimated in a k-th iteration and/or a difference between SPs, $S_{k-1}(i)$, estimated in the k−1-th iteration and SPs, $S_k(i)$, estimated in the k-th iteration falls within a preset range.

When the difference between TCs, $A_{k-1}(i)$, estimated in the k−1-th iteration and TCs, $A_k(i)$, estimated in the k-th iteration and the difference between SPs, $S_{k-1}(i)$, estimated in the k−1-th iteration and SPs, $S_k(i)$, estimated in the k-th iteration fall within the preset range, the apparatus 400 may determine the second TCs, $A_k(i)$, and SPs, $S_k(i)$, estimated in the k-th iteration as activation patterns for the target object.

On the other hand, when the difference between TCs, $A_{k-1}(i)$, estimated in the k−1-th iteration and TCs, $A_k(i)$, estimated in the k-th iteration and/or the difference between SPs, $S_{k-1}(i)$, estimated in the k−1-th iteration and SPs, $S_k(i)$, estimated in the k-th iteration is not within the preset range, the apparatus 400 may iteratively perform an operation of estimating activation patterns for the target object.

In another exemplary embodiment, the apparatus 400 may iterate the estimation of activation patterns for the target object a predetermined number of times.

The number of iterations of the estimation may be determined by a user in consideration of the length of time that the user or participant can wait, or may be a prestored value. Alternatively, the number of iterations may vary adaptively depending on whether the result of estimation obtained by iterative learning satisfies a predetermined condition.

The apparatus 400 according to an exemplary embodiment may determine the first TCs and the first SPs as initial values $A0(i)$ and $S0(i)$ of the TCs and SPs estimated for the target object, respectively, and iteratively perform the estimation of activation patterns for the target object a predetermined number of times.

For illustrative purposes, it is assumed that the predetermined number of iterations is n.

In a k-th iteration (k is in integer, k<n+1), the apparatus 400 may newly estimate TCs, $A_k(i)$, and SPs, $S_k(i)$, for the target object from the second brain function data by using the TCs, $A_{k-1}(i)$, and SPs, $S_{k-1}(i)$, estimated in a k−1-th iteration.

When k=n, the apparatus 400 may determine the estimated second TCs, $A_k(i)$, and SPs, $S_k(i)$, as activation patterns for the target object. However, when k<n, the apparatus 400 may further iterate the estimation of activation patterns for the target object by using the estimated second TCs, $A_k(i)$, and SPs, $S_k(i)$.

Alternatively, when the result of estimation obtained by n-th iteration does not satisfy a predetermined condition, the apparatus 400 may further iterate the estimation of activation patterns for the target object.

The operation S220 will be described in more detail later with reference to FIG. 3.

Although not shown in FIG. 2, the method of processing a medical image signal according to an exemplary embodiment may further include displaying the estimated second TCs and SPs on a screen.

The apparatus 400 according to an exemplary embodiment uses an iterative DR approach to interpret each individual's BOLD data, thereby allowing more accurate estimation of the individual's brain function activation patterns associated with a task.

In addition, although not shown in FIG. 2, the method may further include determining whether individual-level SPs estimated by using the iterative DR approach are normal.

That is, in the apparatus 400 SPs obtained from a group of normal participants may be acquired in response to the same task as reference activation patterns.

The apparatus 400 may determine the normality of the individual-level SPs based on a confidence interval for the reference activation patterns (e.g., when error probability, i.e., a p-value is less than 0.05). In other words, the apparatus 400 may determine whether the SPs for the target object is normal based on a degree of similarity between the reference activation patterns and the SPs estimated as activation patterns for the target object.

Figure 3:
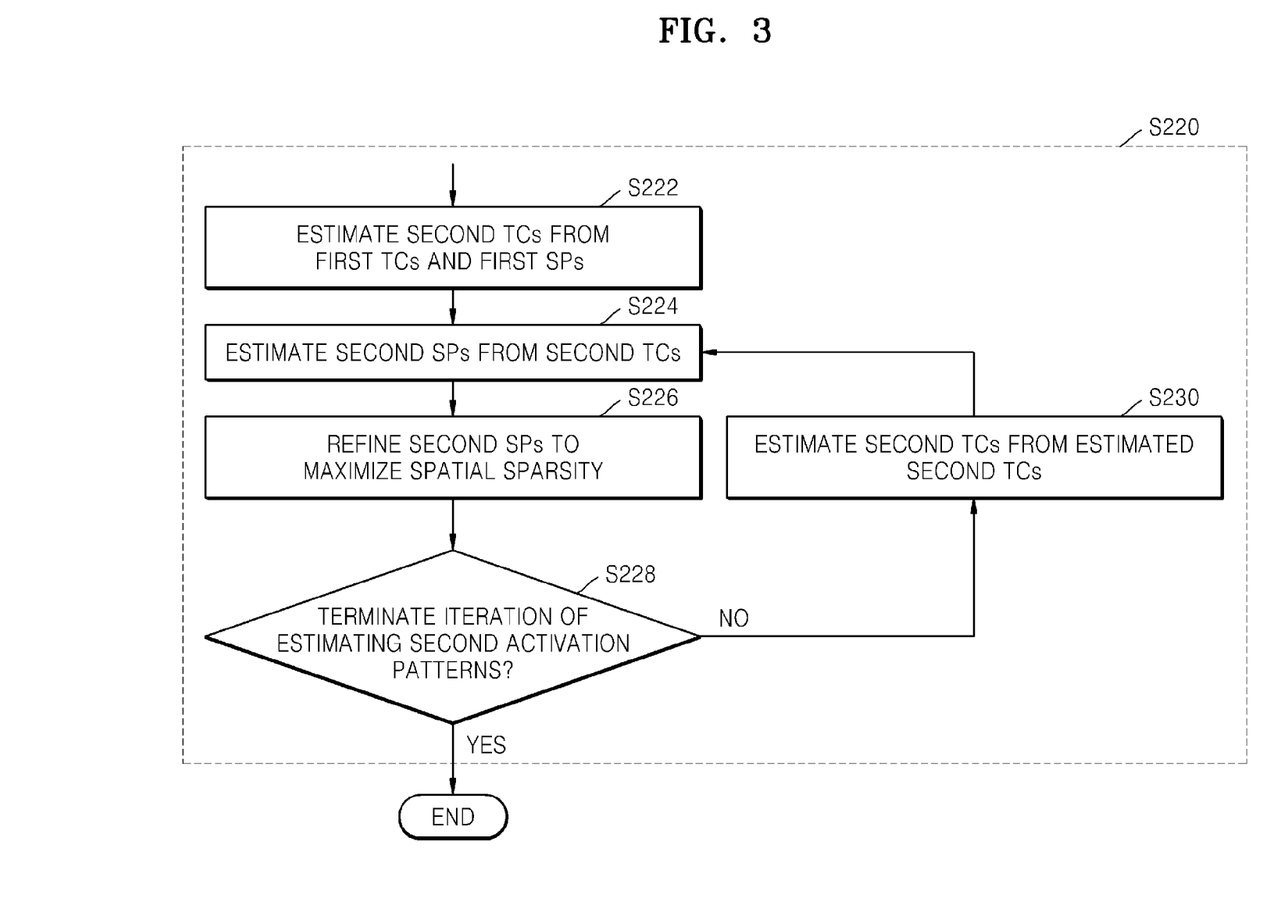
FIG. 3 is a detailed flowchart of an operation of estimating second temporal activation patterns and second spatial activation patterns in the method of FIG. 2.

FIG. 3 is a detailed flowchart for explaining an operation of estimating second TCs and SPs in a method of processing a medical image signal according to an exemplary embodiment.

The operation of estimating the second TCs and SPs will now be described with reference to FIG. 3 and Equations (4) through (6) below. An iterative DR approach is proposed by using the Equations (4) and (5) below.

$$A_k(i)=(1-\alpha)A_{k-1}(i)+\alpha X(i)S_{k-1}(i)^T(S_{k-1}(i)S_{k-1}(i)^T)^{-1} \quad (4)$$

$$\hat{S}_k(i)=(1-\beta)S_{k-1}(i)+\beta(A_k(i)^T A_k(i))^{-1}A_k(i)^T X(i) \quad (5),$$

wherein k (=1, 2, ... ) denotes an iteration number. For example, k may be 100, 200, or 1000, but is not limited thereto.

$A_k(i)$ and $\hat{S}_k(i)$ denote individual-level TCs and SPs for an i-th object, which are estimated in a k-th iteration, respectively.

α and β are parameters that control the amount of updates of individual-level TCs and SPs, respectively, and mean learning rates that control an update speed of iterative learning. The learning rates may be values that generally yield good performance for normalized data, such as $10^{-2}$, $10^{-3}$, $10^{-4}$, and $10^{-5}$, but are not limited thereto.

In addition to applying the iterative DR approach expressed in Equations (4) and (5), the SPs may be additionally refined.

The individual-level SPs estimated by using Equations (4) and (5) may be organized to maintain their independence by maximizing the spatial sparsity of each of the row vectors representing the SPs across voxels within a brain area.

As defined by Equation (6) below, the SPs may be subsequently refined by performing learning using the first-order derivative of Laplacian pdf (i.e., sign function via a gradient descent scheme).

$$S_k(i) = \hat{S}_k(i) - \gamma \text{sign}(\hat{S}_k(i)) \quad (6)$$

wherein γ is a learning rate that controls an update speed of spatial sparsity. For example, γ may be $10^{-2}$, $10^{-3}$, $10^{-4}$, or $10^{-5}$, but is not limited thereto.

The iteration number k and the learning rates α, β, and γ may be input by a user or may be prestored values.

The apparatus 400 applies the iterative DR approach using group-level TCs and SPs as initial values to estimate individual-level TCs and SPs for individual's brain function data.

Returning to FIG. 3, the apparatus 400 estimates second TCs (i.e., individual-level TCs) from the first TCs (i.e., group-level TCs) and the first SPs (i.e., group-level SPs) for a group of multiple objects (S222).

That is, when k=1 in Equation (4) above, the results of the TC-GICA method may be used as initial values A0($i$) and S0($i$)) of the second TCs and the second SPs (i.e., individual-level SPs) for a target object. In other words, the first TCs, A(g), and the first SPs, S(g), acquired in the operation S110 of FIG. 2 may be used as initial values of the second TCs and the second SPs, respectively.

The apparatus 400 estimates second SPs from the second TCs (S224). The operation S224 may be performed by using Equation (5).

The apparatus 400 the refines the estimated second SPs to maximize the spatial sparsity of each of the second SPs (S226). The operation S226 may be performed by using Equation (6).

The apparatus 400 determines whether to iterate the estimation of the second TCs and SPs (S228).

In one exemplary embodiment, the apparatus 400 may determine whether to iterate the estimation of individual-level activation patterns based on whether a difference between activation patterns estimated in the previous iteration and newly estimated activation patterns falls within a preset range.

When a difference between second TCs estimated in the previous iteration and newly estimated TCs or a difference between second SPs estimated in the previous iteration and newly estimated SPs are within the preset range, the apparatus 400 may determine to terminate iterations of the estimation of the second TCs and SPs.

In another exemplary embodiment, the apparatus 400 may determine whether to iterate the estimation of the individual-level activation patterns based on a predetermined number of iterations.

When the apparatus 400 determines to terminate iterations of the estimation of the second TCs and SPs in operation S228, the operation of processing a medical image signal illustrated in FIG. 3 may be terminated.

For example, when the apparatus 400 repeats the estimation of the second TCs and SPs n times, the operation illustrated in FIG. 3 may be terminated.

However, when the apparatus 400 determines not to terminate iterations of the estimation of the second TCs and SPs, the apparatus 400 may estimate second TCs from the estimated and refined second TCs and second SPs obtained in the previous iteration (S230).

For example, in a k-th iteration where k<n+1 and n is a predetermined iteration number, the apparatus 400 may estimate TCs, $A_k(i)$, from TCs, $A_{k-1}(i)$, and SPs, $S_{k-1}(i)$, estimated in a k−1-th iteration by using Equation (4).

FIG. 3 shows that the apparatus 400 repeats the operations S224 and S226 of estimating and refining second SPs by using the second TCs estimated in the operation S230.

For example, in a k-th iteration where k<n+1 and n is a predetermined iteration number, the apparatus 400 may estimate SPs, $S_k(i)$, from the TCs, $A_k(i)$, estimated in the operation S230 by using Equations (5) and (6).

In addition, the apparatus 400 uses the iterative DR approach to fine tune individual-level SPs using updated individual-level TCs.

The apparatus 400 employs an iterative DR approach to estimate brain function activation patterns that are approximated further to individual's brain function data, i.e., individual's BOLD data, and further refine the brain function activation patterns.

Figure 4:
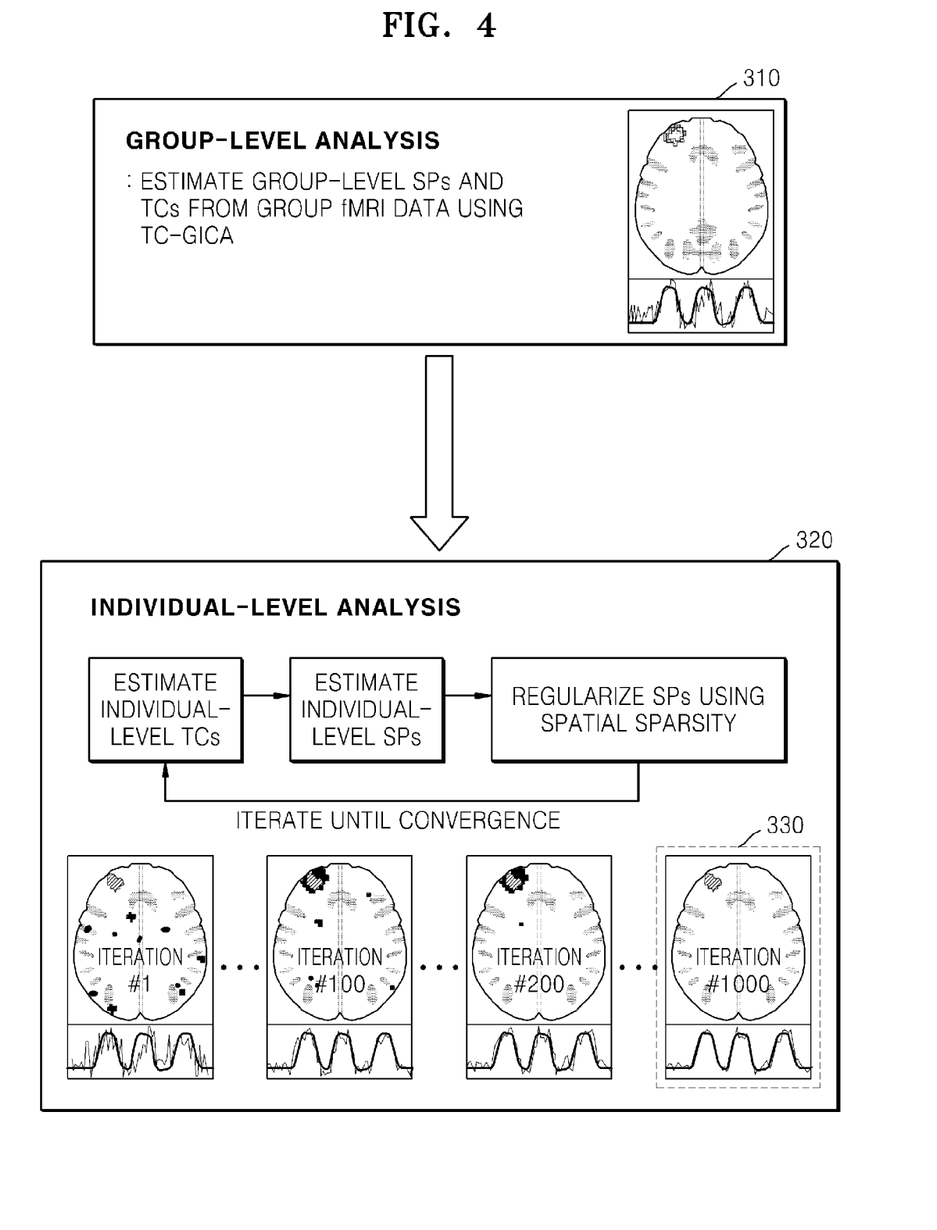
FIG. 4 is a schematic diagram for explaining a method of processing an image signal according to an exemplary embodiment.

FIG. 4 is a schematic diagram for explaining a method of processing an image signal according to an exemplary embodiment. The operation of the apparatus 400 for performing the same method will now be described with reference to FIG. 4.

As illustrated in 310 and 320 of FIG. 4, the apparatus 400 may perform group-level analysis on acquired brain function data, followed by individual-level analysis.

First, as illustrated in 310, the apparatus 400 may estimate group-level SPs and TCs from group fMRI data by using a TC-GICA method. The group-level analysis 310 illustrates an example of the group-level SPs and TCs. Here, the apparatus 400 may estimate individual-level activation patterns more accurately and stably at an early stage of an iterative DR approach by using group-level TCs with group-level SPs as initial values for analyzing individual-level brain function activation patterns.

Next, as illustrated in 320, the apparatus 400 may estimate individual-level SPs by using an iterative DR approach considering spatial sparsity. The apparatus 400 may use the iterative DR approach to reconstruct brain function data from the estimated individual-level activation patterns to be similar to the actually measured brain function data.

The individual-level analysis 320 illustrates an example of individual-level SPs and TCs when an iteration number k is 1, 100, 200, and 1000. As illustrated in 320, as the iteration number k increases, noise in the individual-level SPs decreases, and the estimated TCs converge to reference TCs.

The apparatus 400 may display finally estimated second TCs and SPs on a screen. For example, when the predetermined number of iterations of the estimation operation is 1000, the apparatus 400 may display finally estimated second TCs and SPs 330 on a screen.

The apparatus 400 may accurately estimate each individual's brain function activation patterns related to a task by approximating individual's BOLD data estimated by using an iterative DR approach to actually measured individual's BOLD data.

Furthermore, when applying the iterative DR approach, the apparatus 400 may increase the independence of different brain activation patterns related to a task by considering the spatial sparsity of the individual's brain function activation patterns.

The iterative DR approach minimizes residual noise between the individual's BOLD data estimated by using at least square (LS) method and the actually measured individual's BOLD data.

Thus, when the estimated BOLD data obtained from the estimated individual-level TCs and SPs is approximated to the individual's BOLD data by using an iterative DR approach, the independence of ICs (i.e., TCs and SPs) that has been maximized by an ICA algorithm is increased.

The apparatus 400 may consider the spatial sparsity of SPs to refine the independence among ICs to which an iterative LS method is applied. The apparatus 400 may also reduce the effects of noise present in individual's BOLD data by considering the spatial sparsity of the SPs.

The apparatus 400 also use the result of group-level analysis as initial values. For example, the apparatus 400 may, use as a template, TCs and/or SPs acquired based on BOLD data obtained from a group of healthy objects (e.g., a group of participants determined to have normal brain functions).

Thus, the apparatus 400 may determine how similar brain function activation patterns of a specific participant being diagnosed are to the brain function activation patterns of the group of healthy objects based on the template for the group of healthy objects.

In addition, the apparatus 400 may determine normality and/or abnormality in a participant's brain function depending on whether the similarity between participant's brain function activation patterns and brain function activation patterns of the group of healthy objects falls within a predetermined range.

In other words, the apparatus 400 may have diagnostic criteria in determining the normality and/or abnormality in a brain function of a specific participant being diagnosed by using a method of processing a medical signal according to an exemplary embodiment.

Furthermore, the apparatus 400 may achieve higher performance analysis of each individual's activated brain function region associated with a predetermined task and more accurate detection of an activated brain function region from a patient with functional brain abnormalities. The medical image signal processing method according to an exemplary embodiment may also improve the reliability of diagnosis of abnormalities in a brain function.

The apparatus 400 may also substantially prevent a normal brain function region from being removed during a surgery for removing a patient's defective brain function region.

Figure 5B:
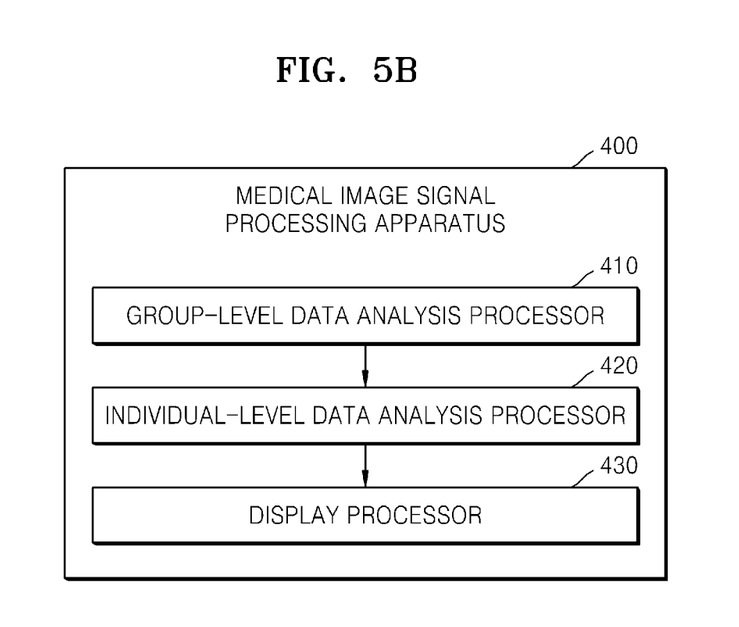

FIGS. 5A and 5B are block diagrams of an apparatus 400 for processing a medical image signal according to exemplary embodiments.

Components in the apparatuses 400 are configured to perform the operations of the method of processing a medical image signal illustrated in FIG. 2. Thus, the above descriptions of the method illustrated in FIG. 2 may also apply to the apparatus 400 of FIGS. 5A and 5B.

Referring to FIG. 5A, the apparatus 400 for processing a medical image signal according to an exemplary embodiment includes a group-level data analysis processor 410 and an individual-level data analysis processor 420. The group-level data analysis processor 410 estimates first TCs and SPs for a group of multiple objects from first brain function data for the group. The individual-level analysis processor 420 estimates second TCs and SPs for a target object from second brain function data obtained from the target object by using the first TCs and SPs. The individual-level analysis processor 420 may iteratively estimate the second TCs and SPs for the target object.

In one exemplary embodiment, the individual-level data analysis processor 420 may acquire third brain function data for the target object from activation patterns estimated in the previous iteration and iteratively perform the operation of estimating activation patterns for the target object until a difference between the second and third brain function data falls within a preset range. In another exemplary embodiment, the individual-level data analysis processor 420 may iteratively perform the operation of estimating activation patterns for the target object for a predetermined number of times.

Referring to FIG. 5B, the apparatus 400 according to an exemplary embodiment includes a group-level analysis processor 410, an individual-level data analysis processor 420, and a display 430. The display 430 may display the activation patterns for the target object, which are determined in the individual-level data analysis processor 420. To this end, the display 430 may include an image generator (not shown) that generates a medical image based on TCs and SPs for the target object estimated in the individual-level data analysis processor 420 and a display (not shown) that displays the generated medical image.

The display 430 may display not only the medical image generated based on the activation patterns for the target object but also status information related to the operation of an fMRI apparatus needed to obtain brain function data and a user interface (UI) or a graphic user interface (GUI) related to setting of functions.

When a touch screen (not shown) including a display panel (not shown) and a touch pad (not shown) in a layer structure is provided, the display 430 may act as an input device as well as an output device. The display 430 may include, for example, a liquid crystal display (LCD), a thin film transistor-LCD (TFT-LCD), an organic light-emitting diode (OLED), a flexible display, a three-dimensional (3D) display, an electrophoretic display. The display 430 may include different types of printers such as inkjet printers and laser printers.

Figure 6:
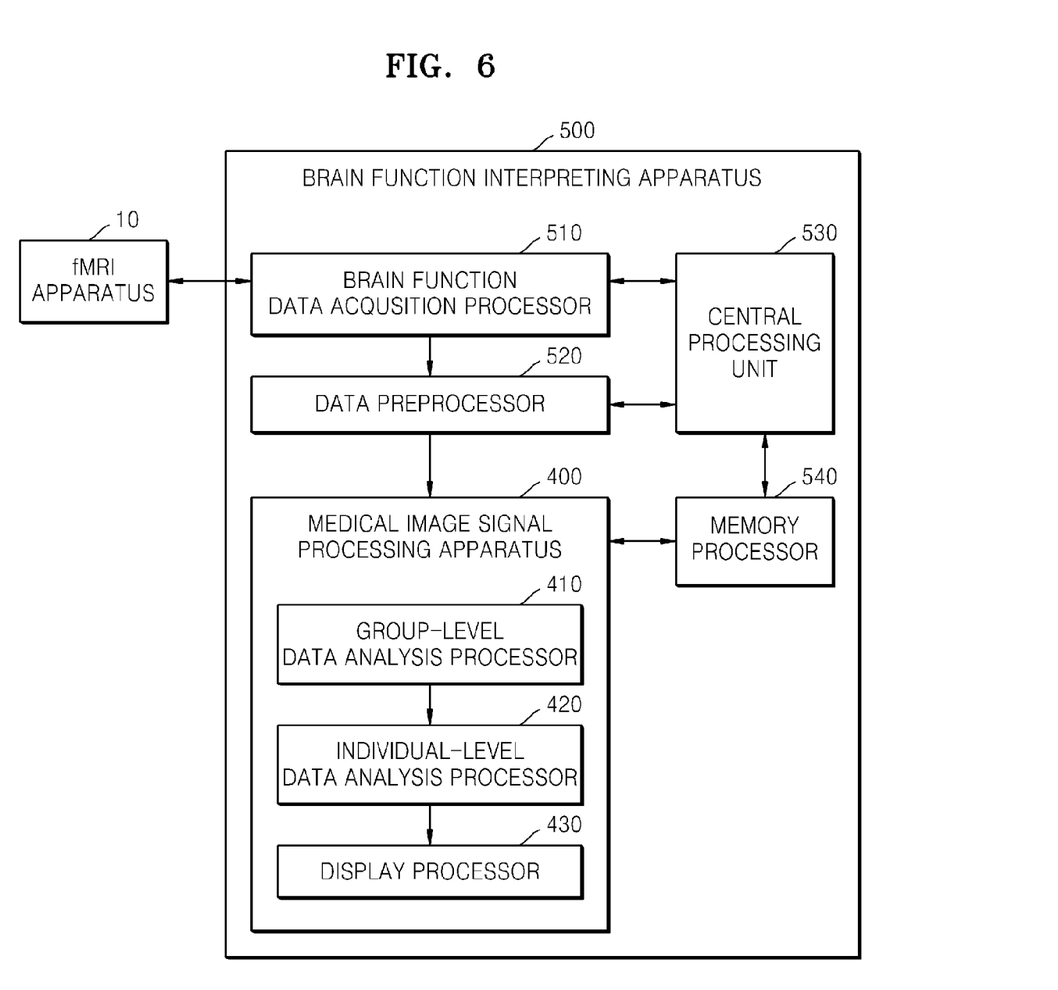
FIG. 6 is a block diagram illustrating an apparatus for interpreting a brain function according to an exemplary embodiment.

FIG. 6 is a block diagram illustrating an apparatus 500 for interpreting a brain function according to an exemplary embodiment. Referring to FIG. 6, the apparatus 500 for interpreting a brain function according to an exemplary embodiment includes the apparatus 400 for processing a medical image signal, a brain function data acquisition processor 510, a data preprocessor 520, a central processing unit (CPU) 530, and a memory 540.

Although not shown in FIG. 6, to achieve a nuclear magnetic resonance (NMR) effect, an fMRI apparatus 10 connected with apparatus 500 may include a magnetic field coil (not shown) for generating a main magnetic field, a gradient field coil (not shown) for generating a magnetic gradient field, and a radio frequency (RF) coil (not shown) for irradiating an object with an RF signal at a resonant frequency and detecting an RF signal reflected from the object. The fMRI apparatus 10 may further include a system controller (not shown) for controlling the magnetic field coil, the gradient field coil, and the RF coil.

The fMRI apparatus 10 generates different types of fMRI data according to a user's request and sends the generated fMRI data to the apparatus 500 for interpreting a brain function. The apparatus 500 may be separate from the fMRI apparatus 10 or may be incorporated into or connected to the fMRI apparatus 10.

The data preprocessor 520 performs preprocessing on brain function data obtained by the brain function data acquisition processor 510, e.g., by refining a movement of an object during measurement or removing noise from the brain function data.

The memory 540 stores programs to be read or processed by the CPU 530. For example, the memory 540 may include a random access memory (RAM) or a read only memory (ROM). In addition, the memory 540 may include a main memory and a sub-memory as separate memories.

The main memory in the memory 540 may include magnetic storage media such as hard disks, floppy disks, and magnetic tapes, optical recording media such as compact disc (CD)-ROMs and digital versatile discs (DVDs), magneto-optical media such as floptical disks, and hardware devices such as ROMs, RAMs and flash memories, which are configured to store and execute program commands.

FIG. 6 shows that the apparatus 400 for processing a medical image signal including the display 430 and the apparatus 500 for interpreting a brain function includes the memory 540. However, in an alternative embodiment, the display 430 may be separate from the apparatus 400 and the memory 540 may be separate from the apparatus 500. That is, the display 430 and the memory 540 may be provided as an independent display and an independent memory, respectively.

The apparatus 500 may be implemented through a computer. Each component in the apparatus 500 may be controlled according to a program for processing a medical image signal that is read from the memory 540 by the CPU 530.

In this case, the computer refers to any device that processes a structured input according to predetermined rules and scrutinizes and outputs the result of the processing. Examples of the computer may include, for example, a general-purpose computer, a supercomputer, a mainframe, a workstation, a microcomputer, and a server. The computer may also include two or more computers (e.g., a distributed computer system) connected together via a communication network such as Intranet, a local area network (LAN), a wide area network (WAN), and a combination thereof.

In addition, medical image signal processing methods according to exemplary embodiments may be embodied in at least one execution program for executing the medical image signal processing methods.

The program for performing the medical image signal processing methods according to exemplary embodiments may be stored in various types of record media. For example, a code for performing the medical image signal processing methods according to exemplary embodiments may be stored in various types of record medium readable by a terminal such as a random access memory (RAM), a flash memory, a read only memory (ROM), erasable programmable ROM (EPROM), an electronically erasable and programmable ROM (EEPROM), a register, a hard disk, a removable disk, a memory card, a universal serial bus (USB) memory, and a compact disc ROM (CD-ROM).

According to exemplary embodiments, an accuracy of estimation of brain function activation patterns from brain function data may be improved, thereby allowing accurate detection of activated brain regions associated with a predetermined task and accurate diagnosis of abnormality in a participant's brain function.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of processing a medical image signal, the method comprising:
   estimating first time courses and first spatial patterns for a group of brain objects from first brain function data for the group; and
   estimating second time courses and second spatial patterns for a target brain object from second brain function data obtained from the target brain object by using the first time courses and the first spatial patterns.

2. The method of claim 1, wherein the estimating the second time courses and the second spatial patterns comprises:
   iteratively estimating time courses $A_k(i)$ and spatial patterns $S_k(i)$ for the target brain object from the second brain function data by using previously estimated time courses $A_{k-1}(i)$ and spatial patterns $S_{k-1}(i)$ for the target brain object,
   wherein the first time courses and the first spatial patterns are used as initial values $A_0(i)$ and $S_0(i)$ of the estimated time courses and spatial patterns for the target brain object respectively, and
   wherein the estimating of the time courses $A_k(i)$ and the spatial patterns $S_k(i)$ is iterated until at least one from among a difference between the previously estimated time courses $A_{k-1}(i)$ and the estimated time courses $A_k(i)$ and a difference between the previously estimated spatial patterns $S_{k-1}(i)$ and the estimated spatial patterns $S_k(i)$ fall within a range.

3. The method of claim 1, wherein the estimating the second time courses and the second spatial patterns comprises:
   iteratively estimating time courses $A_k(i)$ and spatial patterns $S_k(i)$ for the target brain object from the second brain function data by using previously estimated time courses $A_{k-1}(i)$ and spatial patterns $S_{k-1}(i)$ for the target brain object,
   wherein the first time courses and the first spatial patterns are used as initial values $A_0(i)$ and $S_0(i)$ of the estimated time courses and spatial patterns for the target brain object, respectively, and
   wherein the estimating of the time courses $A_k(i)$ and the spatial patterns $S_k(i)$ for the target brain object is iterated a number of times.

4. The method of claim 1, wherein the estimating the second time courses and the second spatial patterns comprises:
   estimating the second time courses from the second brain function data, the first time courses, and the first spatial patterns; and
   estimating the second spatial patterns from the second brain function data and the second time courses.

5. The method of claim 4, wherein the estimating the second time courses and the second spatial patterns further comprises refining the estimated second spatial patterns to maximize independence of each spatial pattern included in the second spatial patterns.

6. The method of claim 1, further comprising displaying the second time courses and the second spatial patterns.

7. The method of claim 1, wherein the estimating the first time courses and the first spatial patterns comprises estimating the first time courses and the first spatial patterns by using a temporal concatenation group independent concatenation analysis (TC-GICA).

8. The method of claim 1, wherein the estimating the first time courses and the first spatial patterns comprises:
generating the first brain function data by concatenating brain function data obtained from each of the brain objects along a time axis; and
estimating the first time courses and the first spatial patterns from the first brain function data by using an independent concatenation analysis (ICA).

9. The method of claim 1, wherein each of the first brain function data and the second brain function data comprises blood oxygenation level dependent (BOLD) data obtained by using a functional magnetic resonance imaging (fMRI) method.

10. The method of claim 1, further comprising:
acquiring spatial patterns obtained from a group of normal participants as reference activation patterns; and
determining whether second spatial patterns determined as activation patterns for the target brain object are normal based on a similarity between the reference activation patterns and the determined second spatial patterns.

11. An apparatus for processing a medical image signal, the apparatus comprising:
a group-level data analysis processor configured to estimate first time courses and first spatial patterns for a group of brain objects from first brain function data for the group; and
an individual-level data analysis processor configured to estimate second time courses and second spatial patterns for a target brain object from second brain function data obtained from the target brain object by using the first time courses and the first spatial patterns.

12. The apparatus of claim 11, wherein the individual-level data analysis processor uses the first time courses and the first spatial patterns as initial values $A_0(i)$ and $S_0(i)$ of time courses and spatial patterns estimated for the target brain object, respectively, and iteratively estimates time courses $A_k(i)$ and spatial patterns $S_k(i)$ for the target brain object from the second brain function data by using previously estimated time courses $A_{k-1}(i)$ and spatial patterns $S_{k-1}(i)$ for the target brain object until at least one from among a difference between the previously estimated time courses $A_{k-1}(i)$ and the estimated time courses $A_k(i)$ and a difference between the previously estimated spatial patterns $S_{k-1}(i)$ and the estimated spatial patterns $S_k(i)$ fall within a range.

13. The apparatus of claim 11, wherein the individual-level data analysis processor uses the first time courses and the first spatial patterns as initial values $A_0(i)$ and $S_0(i)$ of time courses and spatial patterns estimated for the target brain object, respectively, and iteratively estimates, a number of times, time courses $A_k(i)$ and spatial patterns $S_k(i)$ for the target brain object from the second brain function data by using previously estimated time courses $A_{k-1}(i)$ and spatial patterns $S_{k-1}(i)$ for the target brain object.

14. The apparatus of claim 11, wherein the individual-level data analysis processor estimates the second time courses from the second brain function data, the first time courses, and spatial patterns, and estimates the second spatial patterns from the second brain function data and the second time courses.

15. The apparatus of claim 14, wherein the individual-level data analysis processor further refines the estimated second spatial patterns to maximize independence of each spatial pattern included in the second spatial patterns.

16. The apparatus of claim 11, further comprising a display configured to display the second time courses and the second spatial patterns.

17. The apparatus of claim 11, wherein the group-level data analysis processor estimates the first time courses and the first spatial patterns by using a temporal concatenation group independent concatenation analysis (TC-GICA).

18. The apparatus of claim 11, wherein the group-level data analysis processor generates the first brain function data by concatenating brain function data obtained from each of the brain objects along a time axis and estimates the first time courses and the first spatial patterns from the first brain function data by using an independent concatenation analysis (ICA).

19. The apparatus of claim 11, wherein each of the first brain function data and the second brain function data comprises blood oxygenation level dependent (BOLD) data obtained by using a functional magnetic resonance imaging (fMRI) method.

20. The apparatus of claim 11, wherein the individual-level data analysis processor acquires spatial patterns obtained from a group of normal participants as reference activation patterns, and determines whether second spatial patterns determined as activation patterns for the target brain object are normal based on a similarity between the reference activation patterns and the determined second spatial patterns.

21. A non-transitory computer-readable recording medium having recorded thereon a program for executing the method of claim 1.

22. An apparatus for processing a medical image signal comprising:
a controller configured to estimate individual-level time courses and corresponding individual-level spatial patterns of a target object from group-level function data of a group of objects,
wherein the controller iteratively estimates the individual-level time courses and the individual-level spatial patterns of the target object using previously estimated time courses and spatial patterns for the target object until the estimated spatial patterns converge within a threshold.

23. The apparatus of claim 22, wherein the individual-level time courses and corresponding individual-level spatial patterns are estimated from the group-level function data by using a temporal concatenation group independent concatenation analysis (TC-GICA).

* * * * *